United States Patent

Czernecki et al.

[11] Patent Number: 5,356,420
[45] Date of Patent: Oct. 18, 1994

[54] DEVICE FOR PUNCTURING

[75] Inventors: Andrzej Czernecki; Dariusz Firchal; Marek Królikowski, all of Warsaw, Poland

[73] Assignee: Przedsiebiorstwo Zagraniczne HTL, Warsaw, Poland

[21] Appl. No.: 96,417

[22] Filed: Jul. 26, 1993

[30] Foreign Application Priority Data

Aug. 3, 1992 [PL] Poland .................. 295552

[51] Int. Cl.$^5$ ............................... A61B 17/34
[52] U.S. Cl. ............................ 606/182; 606/181
[58] Field of Search .................. 606/181–189; 604/136, 157; 128/907

[56] References Cited

U.S. PATENT DOCUMENTS

| | | | |
|---|---|---|---|
| 4,139,011 | 2/1979 | Benoit et al. | 606/182 |
| 4,203,466 | 5/1980 | Höfert et al. | 606/182 |
| 4,388,925 | 6/1983 | Burns | 606/182 |
| 4,527,561 | 7/1985 | Burns | 606/182 |
| 4,624,253 | 11/1986 | Burns | 606/181 |
| 4,653,513 | 3/1987 | Dombrowski | 606/182 |
| 4,817,603 | 4/1989 | Turner et al. | 606/182 |
| 4,889,117 | 12/1989 | Stevens | 606/181 |
| 4,976,724 | 12/1990 | Nieto et al. | 606/181 |
| 5,026,388 | 6/1991 | Ingalz | 606/182 |
| 5,147,375 | 9/1992 | Sullivan | 606/182 |

*Primary Examiner*—Ralph Lewis
*Attorney, Agent, or Firm*—Michael D. Bednarek

[57] ABSTRACT

A puncturing device which includes a sleeve (1), a push-button (2) mounted on one end of the sleeve (10), a piston (5) which has a puncturing tip (7) and is mounted in the sleeve (1), and a power spring (9) placed inside the sleeve (1) between the face (8) of the push-button (2) and the piston (5). The piston (5) has on its outside perimeter wings (11) which rest against the internal projection (12) of the sleeve (1). A return spring (10) is located inside the sleeve (1) between its bottom (3) with the hole (4) for the puncturing tip (7) and the piston (5).

13 Claims, 1 Drawing Sheet

DEVICE FOR PUNCTURING

FIELD OF THE INVENTION

The present invention is directed to a device for puncturing, in particular for puncturing of the finger, the ear or the heel of a patient in order to take a blood sample for diagnostic purposes.

BACKGROUND OF THE INVENTION

A disposable lancet designed for puncturing the skin of a patient's finger and enabling the taking of a blood sample is known from U.S. Pat. No. 4,889,117. The lancet is made of a long and stiff shank which exhibits on one of its ends a puncturing tip in the shape of a subcutaneous needle. At the other end the shank is joined with a capsule. The shank is slidably mounted along the entire length in a sleeve which is partially located in the capsule. A spring is located between the sleeve and the bottom of the capsule. By holding the sleeve opening against the patient's finger and pressing the capsule, the sleeve is caused to overcome the action of the spring and move toward the bottom of the capsule by a set distance sufficient to puncture the skin of the patient's finger with the puncturing tip mounted on the shank. After the lancet is used the puncturing tip retreats completely into the sleeve and the capsule element protruding inside it makes it impossible to reuse the lancet.

A finger puncturing device made up of a sleeve inside which a spring is mounted by one end is also known from the Polish disclosure document no. P.293343. On the other end of the spring, a piston with a puncturing tip is slidably mounted in the sleeve and supported by the trigger catch. After pressing the trigger, the catch releases the piston equipped with the puncturing tip and the decompressing spring causes the piston to hit the bottom of the sleeve, and the puncturing tip passing through the hole in the bottom of the sleeve punctures the patient's finger. After that the spring returns to the rest position, in which the puncturing tip is completely hidden inside the sleeve.

SUMMARY OF THE INVENTION

The puncturing device according to invention comprises a sleeve, a push-button mounted on one end of the sleeve, a piston which is slidably mounted in the sleeve and has a puncturing tip, and a power spring placed inside the sleeve between the face of the push-button and the piston. The device is characterized by the fact that, on its outer perimeter, the piston has wings which rest against an internal projection of the sleeve, and that a return spring is placed inside the sleeve between its bottom with a hole for the puncturing tip and the piston.

The device according to invention enables quick and relatively painless piercing of the puncturing surface of the patient. By virtue of its construction, the device is disposable, because after breaking off the piston wings it can not be reused. The application of such a device eliminates or significantly reduces the risk of accidental puncturing of skin by the person taking the blood, and this limits the danger of transmitting blood diseases from the patient, who is a carrier of infected blood, to the person who is taking the blood or to a second patient.

BRIEF DESCRIPTION OF THE DRAWINGS

The object of invention is presented based on an exemplary embodiment shown in the drawings, in which.

DETAILED DESCRIPTION OF THE DRAWINGS

Figure 1:
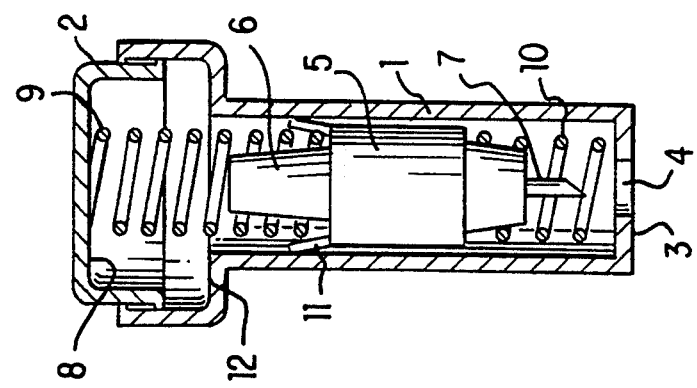
FIG. 1 illustrates the longitudinal section of the device before use.
Figure 2:
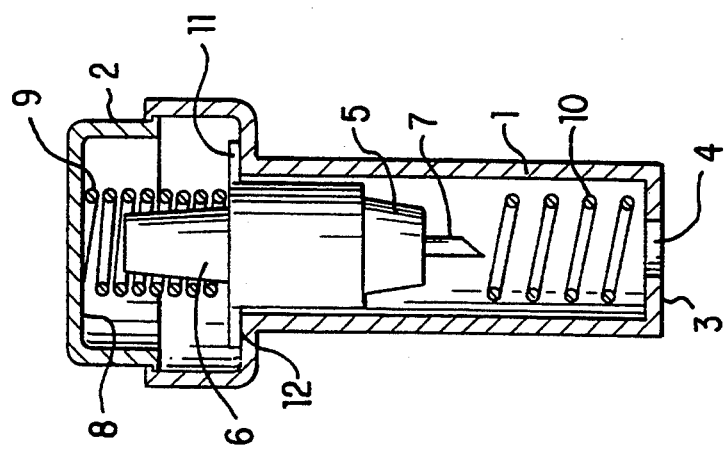
FIG. 2 shows the longitudinal section of the device after use.

As shown in FIGS. 1 and 2, the puncturing device is made of a sleeve 1 and a push-button 2 mounted on one end of the sleeve 1. The second end of the sleeve 1 terminates in a bottom 3 with a hole 4. The piston 5 is slidably mounted inside the sleeve 1. The piston 5 terminates with a pusher 6 on the side of the push-button 2, and on the side of the hole 4 in the bottom 3 of the sleeve 1, the piston terminates with a puncturing tip 7. A power spring 9 is placed inside the sleeve 1 between the face 8 of the push-button 2 and the piston 5, while a return spring 10 is placed between the piston 5 and the bottom 3 of the sleeve 1. On its external perimeter the piston 5 has wings 11 which rest against the internal projection 12 of the sleeve 1.

The device operates as follows. The positioning of the device elements before use is shown in FIG. 1. Due to the pressure exerted by the power spring 9, the wings 11 of the piston 5 rest against the projection 12 of the sleeve 1 keeping the piston 5 with the puncturing tip 7 in the first stable position. Pressing on the push-button 2 causes compression of the power spring 9 until the moment when the face 8 of the push-button 2 pushes against the pusher 6 of the piston 5. Continuing to press the push-button 2 causes the wings 11 of the piston 5 to break off, such that the power spring 9 drives the piston 5. The puncturing tip 7 passes through the hole 4 in the bottom 3 of the sleeve 1 and pierces the puncturing surface. After this, the return spring 10 withdraws the piston 5 with puncturing tip 7, which assumes a stable position inside the sleeve 1. The positioning of device elements after its use is show in FIG. 2. It is impossible to reuse the device when the wings 11 are broken off.

Other embodiments are naturally possible. For example, the pusher 6 can constitute a part of the push-button 2 which drives the piston 5 inside the sleeve 1.

What is claimed is:

1. A puncturing device comprising: a sleeve having a top end and a bottom end, the bottom end having a hole formed therein; a push-button mounted at the top end of the sleeve and slidable with respect to the sleeve, the push button having an inner face; a piston which is slidably mounted in the sleeve; a power spring placed inside the sleeve between the inner face of the push-button and the piston; wherein the piston is provided with a puncturing tip at one end and at least one frangible wing projecting radially outward from the piston outer perimeter, the wing resting against an internal projection of the sleeve to restrict the range of sliding of the piston within the sleeve such that the puncturing tip is maintained within the sleeve; and a return spring placed inside the sleeve between the sleeve's bottom and the piston for biasing the puncturing tip back into the sleeve when the frangible wing is broken.

2. The puncturing device of claim 1, wherein the piston is provided with a plurality of frangible wings resting against the internal projection of the sleeve, each of the frangible wings projecting radially outward from the piston.

3. The puncturing device of claim 1, wherein the return spring is spaced from and not in contact with the piston until the frangible wing is broken.

4. The puncturing device of claim 1, wherein the sleeve comprises a first cylindrical portion having a predetermined inner diameter and a second cylindrical portion having a predetermined inner diameter which is less than the inner diameter of the first cylindrical portion and wherein the internal projection is an annular flange extending radially inward from the first cylindrical portion to connect the first cylindrical portion to the second cylindrical portion.

5. The puncturing device of claim 4, wherein the first cylindrical portion, the second cylindrical portion and the annular flange are all integrally formed as a single piece.

6. The puncturing device of claim 4, wherein the piston has an outer periphery having a predetermined diameter which is less than the diameter of the second cylindrical portion such that the piston can slide within the second cylindrical portion, but wherein the frangible wing projects radially outward beyond the first cylindrical portion and is biased against the annular flange by the power spring to restrict the range of sliding of the piston within the sleeve such that the puncturing tip is maintained within the sleeve.

7. The puncturing device of claim 1, wherein the device includes the following five pieces: a one-piece sleeve, a one-piece push button, a one-piece piston with puncturing tip and frangible wing, a one-piece power spring and a one-piece return spring.

8. A puncturing device comprising: a sleeve having first and second ends and an internal projection located between the first and second ends and a hole formed at the second end of the sleeve; a piston slidably mounted within the sleeve, the piston having two ends and including a puncturing tip provided at one end and a plurality of frangible wings projecting radially outward from the piston and resting against the internal projection of the sleeve to restrict the range of sliding of the piston within the sleeve such that the puncturing tip is maintained within the sleeve; a push button located proximate the first end of the sleeve and being slidable with respect to the sleeve for pushing against the end of the piston opposite the end having the puncturing tip; a first spring for biasing the push button away from the piston, the first spring being arranged such that when the push button is pressed against the bias of the first spring into contact with the piston far enough to break the wings of the piston, the first spring acts to push the piston toward the second end of the sleeve so that the puncturing tip extends out of the hole formed in the second end of the sleeve; and a second spring located between the end of the piston having the puncturing tip and the second end of the sleeve for biasing the puncturing tip back into the sleeve.

9. The puncturing device of claim 8, wherein the second spring is spaced from and not in contact with the piston until the frangible wings are broken.

10. The puncturing device of claim 8, wherein the sleeve comprises a first cylindrical portion having a predetermined inner diameter and a second cylindrical portion having a predetermined inner diameter which is less than the inner diameter of the first cylindrical portion and wherein the internal projection is an annular flange extending radially inward from the first cylindrical portion to connect the first cylindrical portion to the second cylindrical portion.

11. The puncturing device of claim 10, wherein the first cylindrical portion, the second cylindrical portion and the annular sleeve are all integrally formed as a single piece.

12. The puncturing device of claim 10, wherein the piston has an outer periphery having a predetermined diameter which is less than the diameter of the second cylindrical portion such that the piston can slide within the second cylindrical portion, but wherein the frangible wing projects radially outward beyond the first cylindrical portion and is biased against the annular flange by the power spring to restrict the range of sliding of the piston within the sleeve such that the puncturing tip is maintained within the sleeve.

13. The puncturing device of claim 8, wherein the device includes the following five pieces: a one-piece sleeve, a one-piece push button, a one-piece piston with puncturing tip and frangible wing, a one-piece first spring and a one-piece second spring.

* * * * *